United States Patent
Baek

(10) Patent No.: US 11,471,136 B2
(45) Date of Patent: Oct. 18, 2022

(54) BIOPSY NEEDLE ASSEMBLY FOR REDUCING STARTING LOAD WHEN MOTOR CHANGES DIRECTION

(71) Applicant: WOON'S MEDICAL INC., Seongnam-si (KR)

(72) Inventor: Woon Baek, Seongnam-si (KR)

(73) Assignee: WOON'S MEDICAL INC., Seongnam-si (KR)

( * ) Notice: Subject to any disclaimer, the term of this patent is extended or adjusted under 35 U.S.C. 154(b) by 451 days.

(21) Appl. No.: 16/623,464

(22) PCT Filed: Jun. 18, 2018

(86) PCT No.: PCT/KR2018/006867
§ 371 (c)(1),
(2) Date: Dec. 17, 2019

(87) PCT Pub. No.: WO2018/236113
PCT Pub. Date: Dec. 27, 2018

(65) Prior Publication Data
US 2021/0145418 A1    May 20, 2021

(30) Foreign Application Priority Data
Jun. 19, 2017  (KR) .................. 10-2017-0077278

(51) Int. Cl.
*A61B 10/02* (2006.01)
*A61B 17/32* (2006.01)

(52) U.S. Cl.
CPC .... *A61B 10/0266* (2013.01); *A61B 17/32002* (2013.01); *A61B 2017/320064* (2013.01)

(58) Field of Classification Search
CPC ............ A61B 10/0266; A61B 10/0233; A61B 2010/0208; A61B 17/32002; A61B 2017/320064; A61B 2017/00398
See application file for complete search history.

(56) References Cited

FOREIGN PATENT DOCUMENTS

| JP | 4754474 | 8/2011 |
|---|---|---|
| JP | 6001120 | 10/2016 |
| KR | 10-2003-0040943 | 5/2003 |
| KR | 10-2016-62199 | 6/2016 |
| KR | 10-1688967 | 12/2016 |

*Primary Examiner* — Devin B Henson
(74) *Attorney, Agent, or Firm* — Lex IP Meister, PLLC

(57) ABSTRACT

The present invention relates to a biopsy needle assembly and, more specifically, to a structure of a biopsy needle assembly for reducing a starting load which improves vibration and noise during a procedure and minimizes irritation to a lesion by, when a motor is operated to move a cutter forward/backward while rotating the cutter, stopping motor rotation and reducing an instantaneous load during an initial operation so as to reduce a firing (starting) load of the motor.

6 Claims, 13 Drawing Sheets

BIOPSY NEEDLE ASSEMBLY FOR REDUCING STARTING LOAD WHEN MOTOR CHANGES DIRECTION

TECHNICAL FIELD

The present invention relates to a biopsy needle assembly and, more particularly, to a biopsy needle assembly able to reduce the starting load of a motor when the direction of the motor is converted to perform translation motion by advancing and retreating a cutter while rotating the cutter to cut a tissue of a living body in a biopsy device used to excise the tissue, such that the reduced starting load of the motor can reduce vibration and noise, thereby reducing the pain of a patient during a surgery.

BACKGROUND ART

In an apparatus or device for performing a surgery by cutting out a portion of tissue of a living body or an affected tissue to inspect the tissue of the living body, a needle assembly has been used to be inserted into the tissue or the affected tissue of the living body. To excise a portion of tissue, a needle is inserted into an affected tissue of a living body, and a cutter rotates while advancing and retreating (translation motion) to excise the portion of the tissue introduced into the needle through an opening of the needle.

Regarding the operation of such a cutter, WO2011/022122 (Feb. 24, 2011) will be described. The translation motion of the cutter is enabled by in response to force, generated by a motor disposed inside of a holster of a body, being transmitted to the cutter via a shaft and gears. FIG. 1 is a side cross-sectional view illustrating a biopsy device including a holster and a probe separate from the holster, and FIG. 2 is an exploded view of the biopsy device, from which housing components, a battery, and a circuit board are removed, and some portions of which are illustrated in cross-sections. FIGS. 1 and 2 correspond to FIGS. 3 and 4 of the specification of WO2011/022122 (Feb. 24, 2011). With reference to these drawings, portions related to the present invention will only be described. As illustrated in FIGS. 1 and 2, gears 82 and 84 of the holster 14 simultaneously rotate when a motor 36 is started. The gears 82 and 84 engage with gears 86 and 88 of the probe when the probe is coupled to the holster 14, so that the gears 86 and 88 are simultaneously rotated by the motor 36. The operating motor 36 simultaneously rotates a hex nut 100 and a worm nut 120. Even though the rotation of a lead screw 122 is driven by the rotation of the hex nut 100 and the lead screw 122 and the worm nut 120 are simultaneously rotated in the same direction, a difference in the rotational speed between the lead screw 122 and the worm nut 120 provides a final net result, by which the lead screw 122 rotates with respect to the worm nut 120. This relative rotation provides a translation motion to a cutter 50 when the cutter 50 rotates.

When the motor 36 is operated to rotate the cutter 50 in the counterclockwise direction (when viewed in the direction from a tissue sample holder 40 to the needle 20), the cutter 50 retreats in a proximal direction. When the motor 36 is operated to rotate the cutter 50 in the clockwise direction (when viewed in the direction from a tissue sample holder 40 to the needle 20), the cutter 50 advances in a distal direction. The motor 36 may be reversed to convert between the distal translation motion and the proximal translation motion of the cutter 50, depending on the direction of the rotation of the motor 36. Alternatively, the cutter 50 may be rotated in the counterclockwise direction during the advancement of the cutter 50 and in the clockwise direction during the retreat of the cutter 50.

In the operation of the motor to advance/retreat the cutter as described above, when the motor enters an initial operation stage (or starting stage) after the rotation of the motor has been stopped, vibration and noise may be caused. The vibration or trembling may stimulate an affected portion, which is problematic.

DISCLOSURE

Technical Problem

Accordingly, the present invention has been made keeping in mind the above problems occurring in the prior art, and an object of the present invention is to provide a biopsy needle assembly able to prevent instantaneous load to reduce the inrush (or starting) load of the motor during an initial operation in which the direction of the rotation of the motor is converted after the rotation of the motor has been stopped when the motor is operated motor to advance/retreat a cutter.

Technical Solution

In order to accomplish the above object, the present invention provides a biopsy needle assembly used in a biopsy device. The biopsy device includes: a body (or motor unit) controlling a motor and a vacuum pressure; a biopsy needle assembly receiving rotational power from the body (or motor unit); and a needle provided on a distal end of the biopsy needle assembly to extend from a cutter that incises a tissue. The biopsy needle assembly includes: a gear unit including a fixed shaft (or primary) gear and a variable shaft (secondary) gear transmitting the rotational power of the motor; a sleeve including one portion connected to a central portion of the variable shaft gear to serve as a shaft of the variable shaft gear, the other portion connected to the cutter, and a thread-shaped screw provided on an outer surface of an intermediate portion between one portion and the other portion of the sleeve; a sleeve moving unit corresponding to a thread of the screw to serve as a nut of the screw to linearly move the sleeve in forward and backward directions; a pair of sleeve supporting units respectively including a compression spring and a pair of spring guides disposed on both sides of the compression spring to face each other, the spring guides defining a gap therebetween due to elastic force of the compressing spring to prevent the compression spring from being in contact with the screw, wherein the pair of sleeve supporting units is fitted around outer surface portions of the sleeve and disposed on both sides of the sleeve moving unit such that the sleeve supporting units to face each other; and a gear support allowing the variable shaft gear to rotate without advancing or retreating and a support supporting and restraining the sleeve moving unit and the sleeve supporting units to be axially movable in a range of the gap between the spring guides defined by the compression spring in a situation in which the sleeve is inserted into the sleeve moving unit and the sleeve supporting units on both sides of the sleeve moving unit, wherein the sleeve advances or retreats while rotating about the sleeve moving unit in response to rotation of the gear unit, and one sleeve supporting unit of the sleeve supporting units, to which a direction of rotation of the motor is converted, delays the advancement or retreat of the sleeve by the gap between the spring guides defined by the compression spring, thereby reducing starting load of the motor.

In addition, in the biopsy needle assembly according to the present invention, the sleeve moving unit may linearly move in response to the screw of the sleeve, and the sleeve moving unit may include a ball or a thread to correspond to the screw to serve as a nut corresponding to the screw, the sleeve moving unit being configured so that the ball or the thread does not escape the screw even when the sleeve rotates.

In addition, in the biopsy needle assembly according to the present invention, the sleeve moving unit may include a fixing holder having a rectangular, elliptical, or polygonal cross-sectional shape, the fixing holder being supported by the support so as not to rotate, and a barrel-shaped support holder having a cylindrical, polygonal, or elliptical outer cross-sectional shape having a protrusion or a recess, with a through-hole being provided in a surface portion of the barrel-shaped support holder, and a ball inserted into the through-hole. The fixing holder may surround the support holder and the ball so that the support holder does not rotate along the outer cross-sectional shape of the support holder in a situation in which the ball is inserted into the through-hole; a thread may be provided directly on an inner surface of the fixing holder; or a thread spring may be inserted into the fixing holder, the thread spring having an outer shape corresponding to the inner surface of the fixing holder; and the support may further include a fixing holder support disposed on an inner surface of a housing of the biopsy needle assembly to restrain rotation of the fixing holder.

In addition, in the biopsy needle assembly according to the present invention, the sleeve may have a shaft guide surface provided on one portion and a pipe-shaped one end of the cutter provided on the opposite portion.

The central portion of the variable shaft gear may be inserted into the shaft guide surface to rotate the variable shaft gear, the sleeve and the cutter rotate and move together, a screw having a thread may be axially provided on an outer surface of an intermediate portion between both ends of the sleeve, and free ends having a zero pitch may be provided on both ends of the screw, and when the sleeve moving unit serving as the nut is inserted into the screw to rotate the sleeve, the sleeve may be rotated and moved by a pitch of the screw, and the sleeve rotates without moving on the free ends having the zero pitch of the screw.

In addition, in the biopsy needle assembly according to the present invention, a gear support allowing the variable shaft gear to rotate without movement (advancement or retreat) and a support supporting and restraining the sleeve moving unit and the sleeve supporting units to be axially movable in a range of the gap between the spring guides defined by the compression spring may be provided integrally with an inner surface of a housing of the biopsy needle assembly.

In addition, in the biopsy needle assembly according to the present invention, the sleeve supporting units may respectively include the compression spring and spring guides respectively having an end portion in contact with one end of both ends of the compression spring and a barrel-shaped portion inserted into the compression spring, the spring guides being fitted around the outer surface of the sleeve.

Advantageous Effects

In the biopsy needle assembly according to the present invention, the sleeve moving unit moves the sleeve and the cutter by pushing the sleeve support units in response to changes in the direction of the rotation in forward rotation and backward rotation of the motor to advance and retreat the cutter, so that the gap is defined between the spring guides of one of the sleeve support units. The advancement or retreat of the cutter can be delayed by the gap, thereby advantageously reducing the starting load of the motor.

In addition, the reduced can reduce an amount of starting current of the motor, thereby advantageously reducing noise.

Accordingly, it is possible to advantageously improving the accuracy of a surgery and increasing the lifetime of the motor.

MODE FOR INVENTION

The present invention has been made to reduce the inrush (or starting) load of a motor during an initial operation in which the direction of the rotation of the motor is converted after the rotation of the motor has been stopped during repetition of forward rotation and backward rotation of the motor when the motor is operated to advance/retreat a cutter. Novel components may be used in a process of transmitting power from the motor to the cutter in order to reduce overload.

Hereinafter, reference will be made to embodiments of the present invention in detail, so that a person having ordinary skill in the art to which the present disclosure relates could easily put the present invention into practice. In the following description, detailed descriptions of known functions and components incorporated into the present invention will be omitted in the case in which the subject matter of the present invention is rendered unclear by the inclusion thereof.

Figure 1:
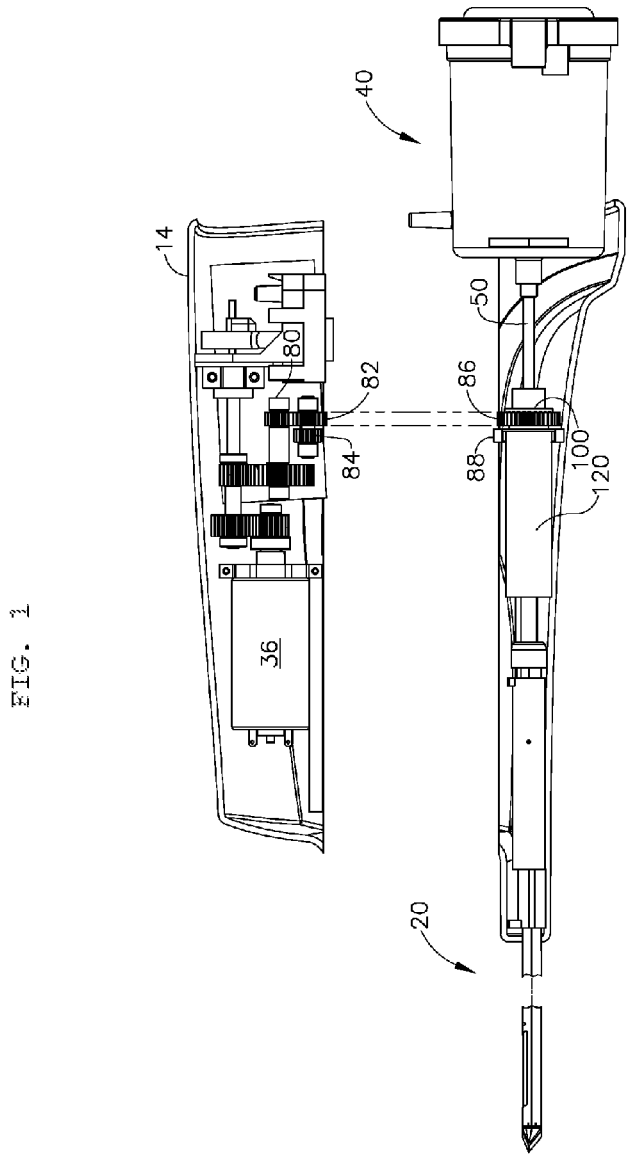
FIG. 1 is a side cross-sectional view illustrating a biopsy device, with a probe thereof being separate from a holster.
Figure 2:
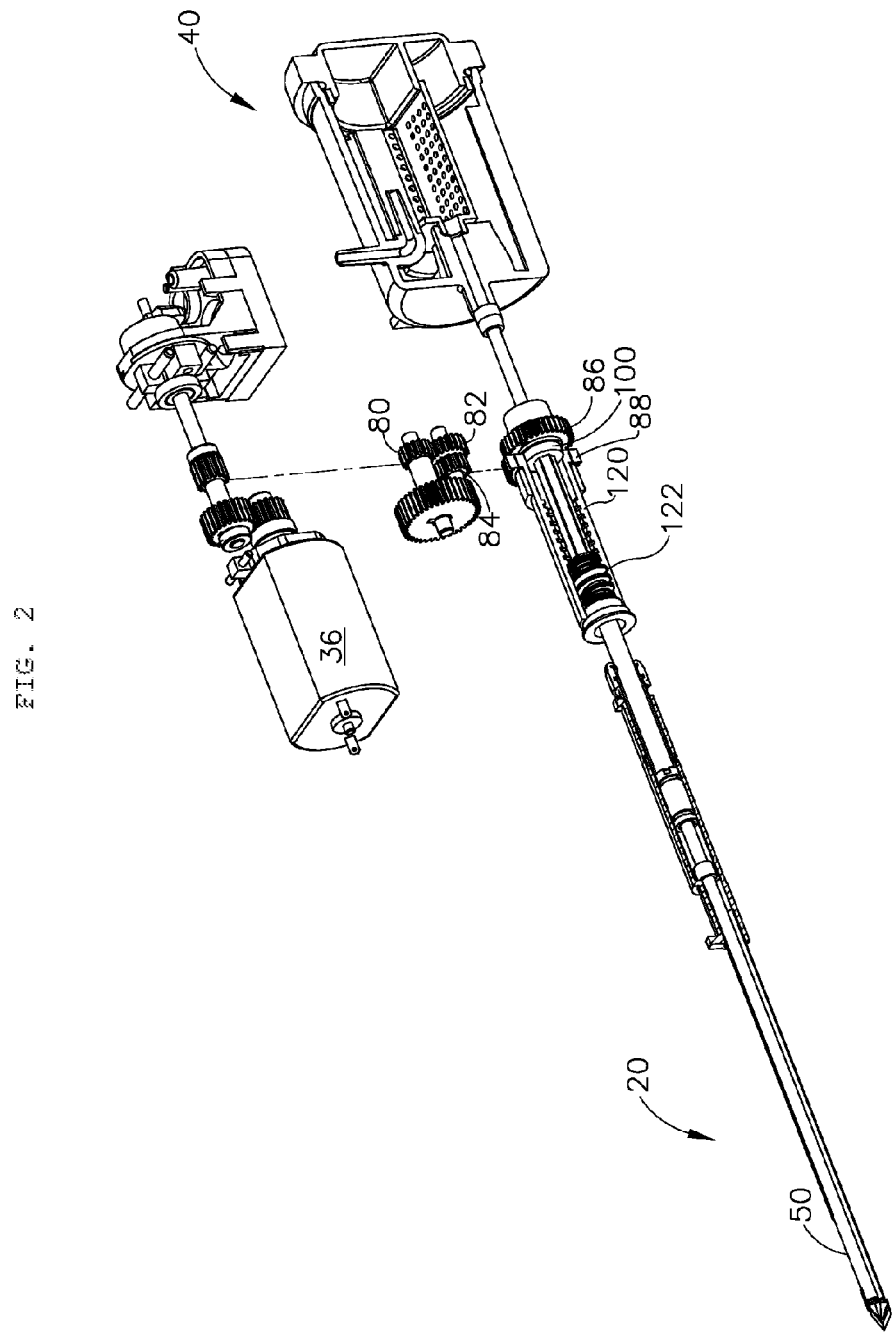
FIG. 2 is an exploded view of the biopsy device, from which housing components, a battery, and a circuit board are removed, and some portions of which are illustrated in cross-sections.
Figure 3:
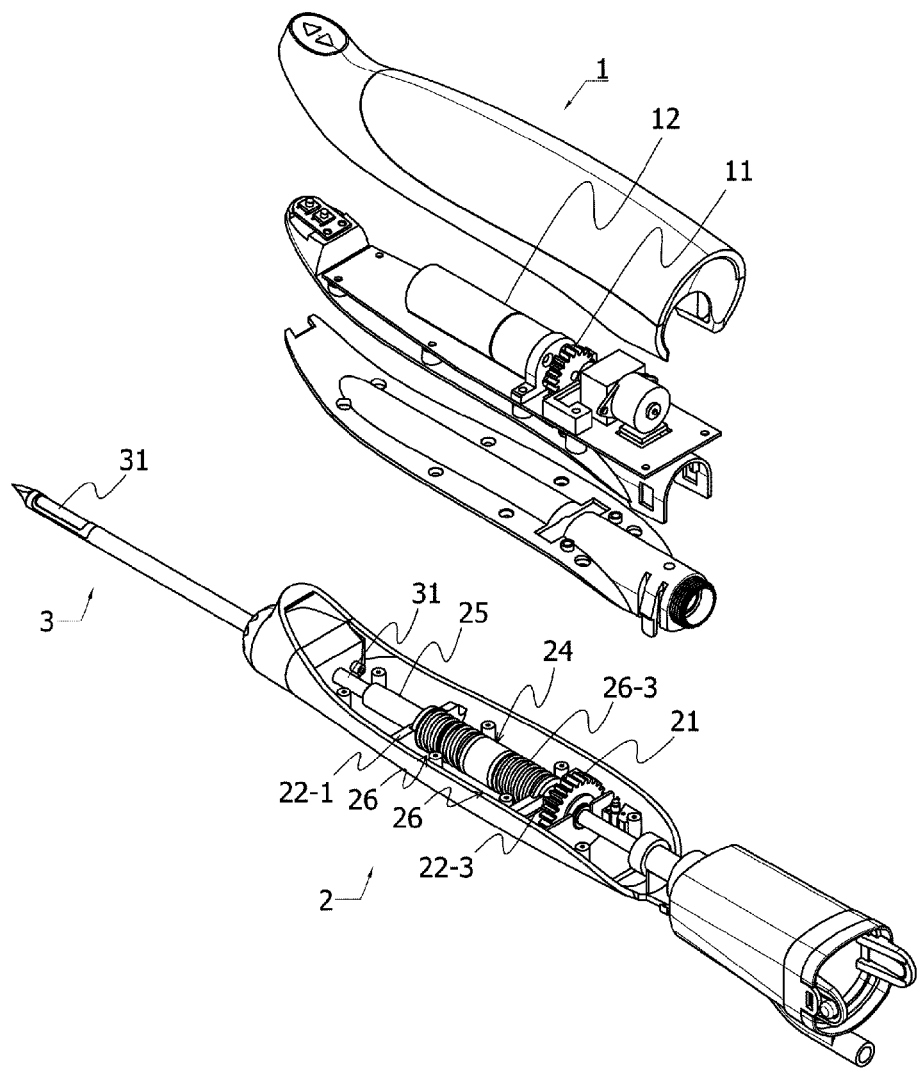
FIG. 3 is an exploded perspective view of the biopsy needle assembly according to the present invention, from which a body (or motor unit) is separated.
Figure 4:
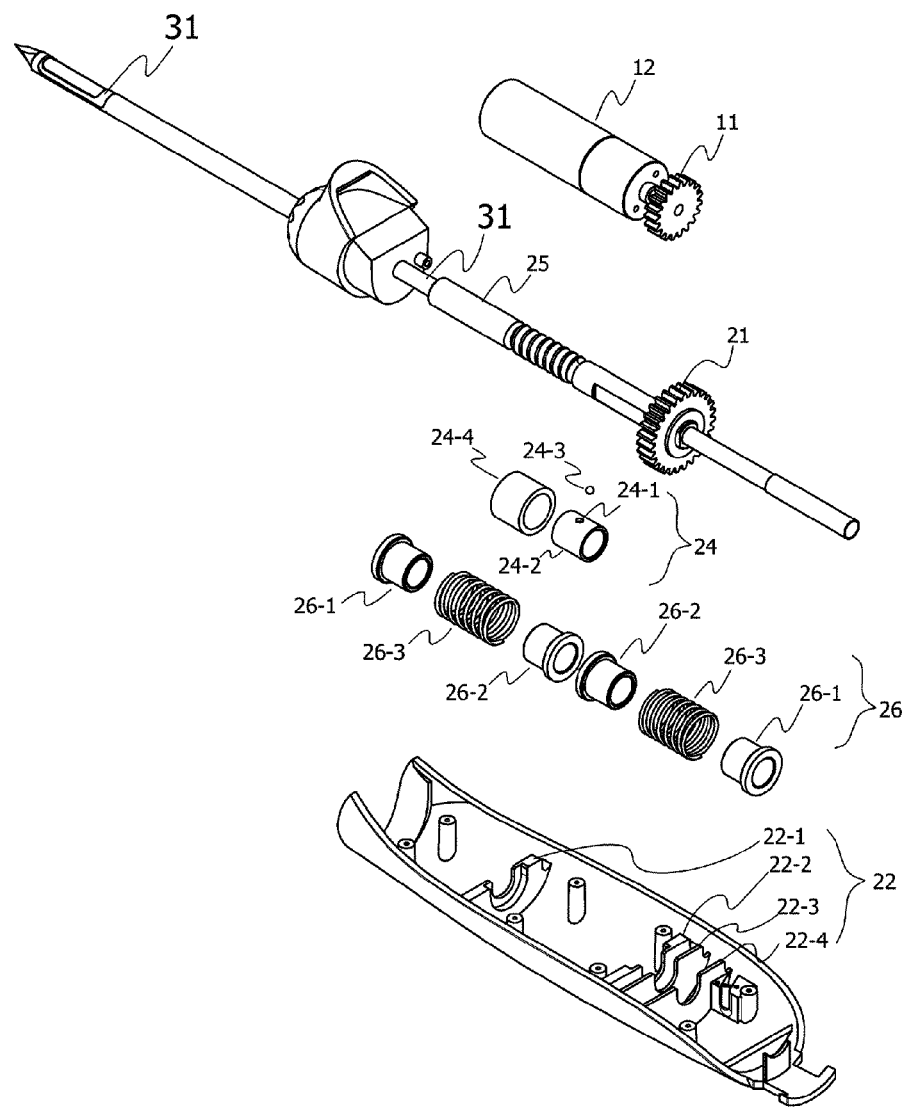
FIG. 4 is an exploded perspective view separately illustrating power transmitting components in FIG. 3.
Figure 5:
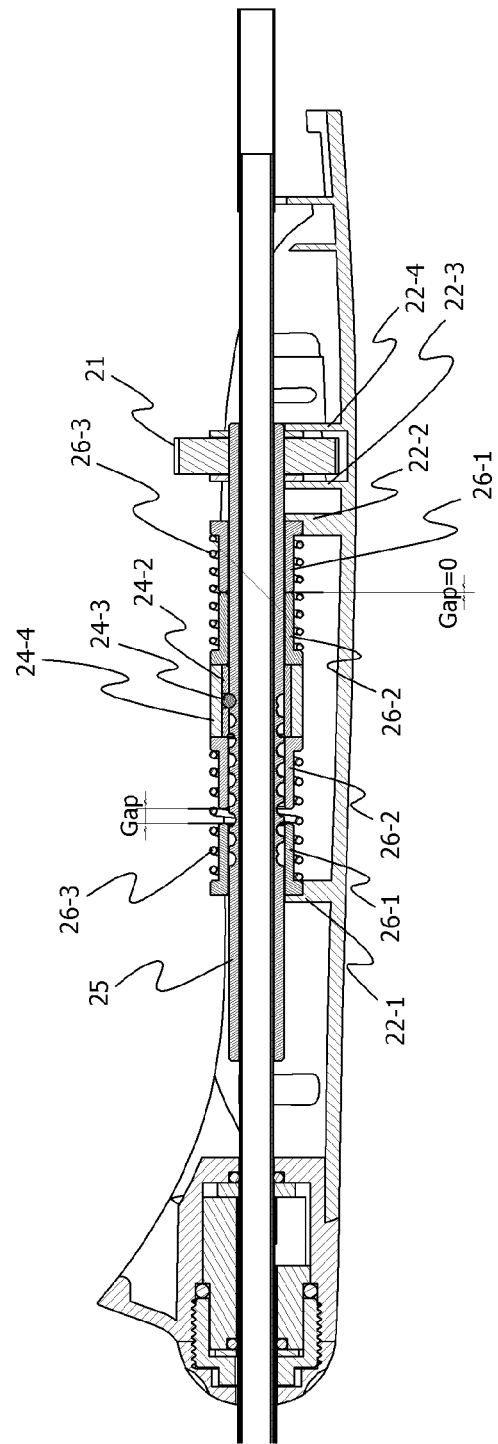
FIG. 5 is a cross-sectional view illustrating portions related to the power transmission of the biopsy needle assembly according to the present invention.

First, a biopsy needle assembly according to a first embodiment of the present invention is illustrated in the following figures, in which FIG. 3 is an exploded perspective view of the biopsy needle assembly according to the present invention, from which a body (or motor unit) is separated, FIG. 4 is an exploded perspective view separately illustrating power transmitting components in FIG. 3, and FIG. 5 is a cross-sectional view illustrating portions related to the power transmission of the biopsy needle assembly according to the present invention.

Describing the principle of the present invention with reference to FIGS. 3 to 5, when the motor generates power by forward or backward rotation in response to a user selecting a switch, the power rotates a fixed shaft gear 11 serving as one component of a power-transmitting gear unit, thereby rotating a variable shaft gear 21 connected to the fixed shaft gear 11, the variable shaft gear 21 serving as another component of the gear unit. The variable shaft gear 21 rotates a sleeve 25 serving as the shaft of the variable shaft gear 21. In response to the rotation of the sleeve 25, a cutter 31 connected to the sleeve 25 advances or retreats.

Here, the connection between the variable shaft gear 21 and the sleeve 25 and the operation of the cutter will be described with reference to FIG. 4.

First, a motor 12 serving as a power source may be caused to rotate at an intended speed using a reducer, or the speed of the motor 12 may be changed to an intended speed using a gear unit comprised of the other gears having different gear ratios. In addition, various types of power or speed transmission methods, known in the art, may be used. The motor 12 and the fixed shaft gear 11 belong to the body 1, and may be used continuously unless broken. In addition, the fixed shaft gear 11 is connected to a gear of a needle 3. In the present invention, the fixed shaft gear 11 is connected to the variable shaft gear 21. A biopsy needle assembly 2 generally used to as a disposable assembly performs power transmission from the fixed shaft gear 11 to the variable shaft gear 21 serving as a secondary gear to which power is transmitted. In the present invention, the variable shaft gear 21 is used as the secondary gear to receive power from the fixed shaft gear 11 serving as a primary gear, which is driven directly by the motor 12. In a case in which a number of gears are connected in a limited space, the overall size of the body 1 may be undesirably increased. Accordingly, the rotation or power of the motor 12 may be transmitted using a planetary reducer or a BLDC motor.

One or more shaft guide surfaces 25-4 are provided on the sleeve 25. The variable shaft gear 21 is axially coupled to the sleeve 25 so as to be movable along the shaft guide surfaces 25-4. The shaft guide surfaces 25-4 allow the sleeve 25 to rotate in response to the rotation of the variable shaft gear 21. The sleeve 25 serves as a spline shaft, while the variable shaft gear 21 serves as a boss of the spline.

Figure 6:
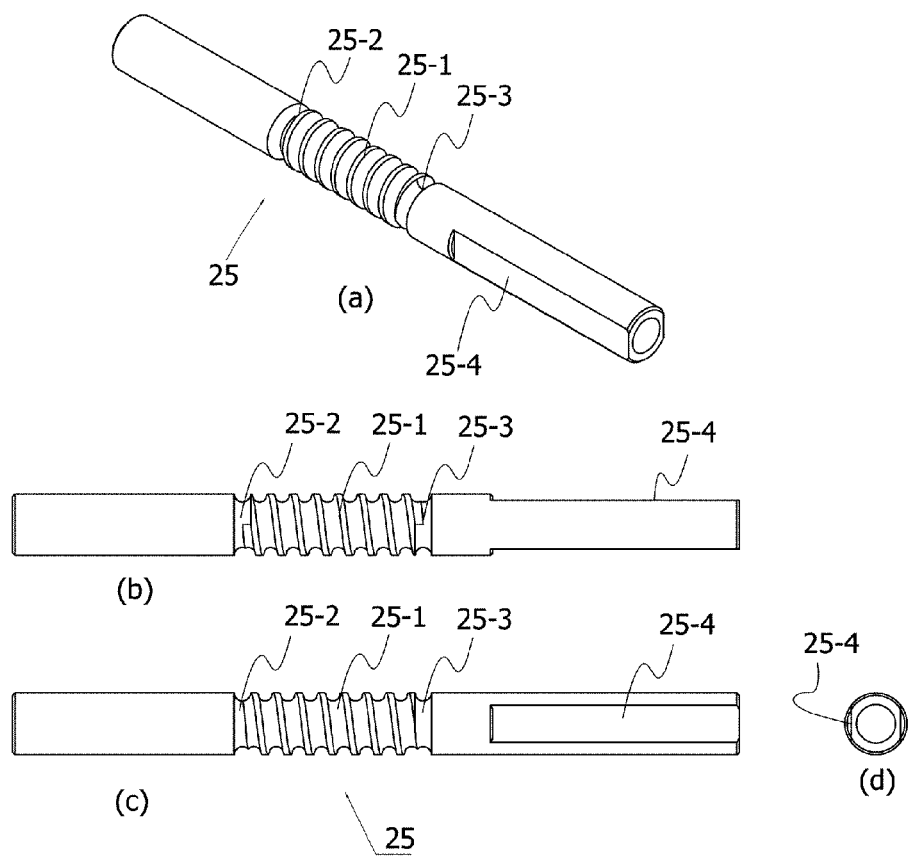
FIG. 6 illustrates a perspective shape, a top shape, a front shape, and a side shape of the sleeve.

FIG. 6 illustrates a perspective shape (a), a top shape (b), a front shape (c), and a side shape (d) of the sleeve. The shaft guide surfaces 25-4 are provided on one portion of the sleeve 25 to serve as the spline together with the variable shaft gear 21, and one end of the cutter 31 is coupled to the other portion of the sleeve 25 so that the cutter 31 rotates or moves together with the sleeve 25. In addition, a spiral-shaped screw 25-1 is provided axially on the outer surface of the sleeve 25 between both ends of the sleeve 25. In addition, free ends 25-2 and 25-3 are provided on both ends of the screw 25-1. The pitch of the free ends is zero (0).

The variable shaft gear 21 is coupled to the shaft guide surfaces 25-4 of one portion of the sleeve 25 such that the sleeve 25 can advance or retreat with respect to the center of the variable shaft gear 21. In addition, the other portion of the sleeve 25 is coupled to the cutter 31 such that the cutter 31 can operate in the same manner as the advancing/retreating movement of the sleeve 25.

In addition, a sleeve moving unit 24 is coupled to the exterior of the screw 25-1.

The sleeve moving unit 24 is trapped and supported by sleeve support units 26 provided on both sides of the sleeve moving unit 24. The sleeve support units 26 may be pressed so that the sleeve 25 can move the cutter 31.

One of the sleeve support units 26, disposed on one side of the sleeve moving unit 24, may be disposed equally on the other side. The sleeve support unit 26, disposed on one side, includes a compression spring 26-3 serving as an elastic member and bobbin-shaped spring guides 26-1 and 26-2 provided on both sides of the compression spring 26-3. Each of the spring guides 26-1 and 26-2 has a support end, to which force from the compression spring 26-3 is applied, and a cylindrical portion, a portion of which is inserted into the inner circumferential surface of the compression spring 26-3.

To perform the above-described function the sleeve moving unit 24 according to the first embodiment includes a cylindrical support holder 24-2 having a through-hole 24-1 provided in an outer portion thereof, a ball 24-3 inserted into the through-hole 24-1 of the support holder 24-2, and a fixing holder 24-4 provided outside of the support holder 24-2 to support the support holder 24-2 and the ball 24-3 in a situation in which the ball 24-3 is inserted into the through-hoe 24-1.

The sleeve moving unit 24 is configured such that the through-hole 24-1 and the ball 24-3 are located above the groove of the screw 25-1 such that the ball 24-3 serves as a thread ridge, thereby serving as a nut corresponding to the screw 25-1. This configuration also prevents the ball 24-3 from escaping the screw 25-1, trapped by the fixing holder 24-4 and the through-hole 24-1 of the support holder 24-2, even when the sleeve 25 is rotated.

The assembly and operation of the sleeve 25, the variable shaft gear 21, and the cutter 31 of the present invention will be described in more detail with reference to FIGS. 3 and 4.

Supports 22 are provided inside of the biopsy needle assembly 2 to fixedly support the spring guide 26-1 of the variable shaft gear 21 and the sleeve support unit 26. The supports 22 may be provided integrally with a housing of the biopsy needle assembly 2.

The variable shaft gear 21 rotates while being trapped by two gear supports 22-3 and 22-4 of the supports 22. Thus, the gear supports 22-3 and 22-4 allow the variable shaft gear 21 to rotate in position, due to torque transmitted to the fixed shaft gear 11. However, the variable shaft gear 21 is spline-coupled to the sleeve 25, such that the sleeve 25 can axially move while rotating together with the variable shaft gear 21. As will be described in more detail later, when the sleeve 25 rotates together with the variable shaft gear 21, the sleeve moving unit 24 coupled to the screw 25-1 of the sleeve 25 functions as a nut and allows the sleeve 25 to move axially.

The sleeve support units 26 respectively include the bobbin-shaped spring guides 26-1 and 26-2 and the compression spring 26-3 fitted into the outer circumferential surfaces of the spring guides 26-1 and 26-2, and are symmetrically provided on both ends of the sleeve moving unit 24. The sleeve support units 26 are provided on the sleeve moving unit 24 to support the sleeve moving unit 24. Here, the two opposite spring guides 26-1 of the sleeve support units 26, not in contact with the sleeve support units 26, are supported by the supports 22-1 and 22-2, respectively, provided on the housing of the biopsy needle assembly 2, so that the sleeve support units 26 support the sleeve moving unit 24.

In particular, as illustrated in FIG. 5, a gap is defined between the spring guide 26-1 and the spring guide 26-2 by the compression spring 26-3.

The variable shaft gear 21 serves as a bobbin of the spline fitted around the shaft guide surfaces 25-4 of the sleeve 25. When the variable shaft gear is caused to rotate, the variable shaft gear can only rotate while being trapped by the gear supports 22-3 and 22-4. The sleeve moving unit 24 is supported by the sleeve support units 26 to be movable within the range of the gap between the spring guide 26-1 and the spring guide 26-2. In addition, the sleeve moving unit 24 is supported by the sleeve support units 26 while being nut-coupled to the screw 25-1. When the sleeve 25 is rotated, the sleeve 25 causes the sleeve moving unit 24 to advance/retreat along the thread of the screw 25-1.

First, when the sleeve moving unit 24 has moved by the gap between the spring guide 26-1 and the spring guide 26-2, the spring guide 26-1 is supported by the supports 22-1 and 22-2, so that the sleeve moving unit 24 cannot advance or retreat. Accordingly, the supports 22-1 and 22-2 limit the movement of the sleeve moving unit 24 and the sleeve support units 26. In particular, while the sleeve support units 26 are moving about the screw 25-1 of the sleeve 25 by the gap together with the sleeve moving unit 24, the sleeve support units 26 are trapped by the supports 22-1 and 22-2 and the movement of the sleeve support units 26 is limited.

The variable shaft gear 21 is fitted around the shaft guide surfaces 25-4 of the sleeve 25 to rotate together with the sleeve 25, and perform a spline movement so that the sleeve 25 can advance and retreat as the shaft of the variable shaft gear 21. In addition, the ball 24-3 is selected depending on the groove of the screw 25-1 of the sleeve 25. When the sleeve 25 advances or retreats, while rotating, about the ball 24-3, the cutter 31 advances or retreats while rotating.

The principle of the operation of the cutter according to the present invention will be described in more detail hereinafter with reference to the first embodiment.

When power is generated by the motor 12 rotating forward or backward in response to a user selecting a switch, the motor 12 rotates the fixed shaft gear 11, which in turn transmits torque to the variable shaft gear 21, thereby continuously rotating the variable shaft gear 21. The variable shaft gear 21 rotates together with the shaft guide surfaces 25-4 of the sleeve 25 while being trapped by the gear supports 22-3 and 22-4. Consequently, the sleeve 25 continuously rotates, and the screw 25-1 of the sleeve 25 rotates about the ball 24-3. Here, the sleeve moving unit 24 moves together with the ball 24-3 to push one end of the spring guide 26-2 of the sleeve support units 26. The gap between the spring guide 26-1 and the spring guide 26-2 is quickly decreased, so that the movement of the sleeve moving unit 24 and the sleeve support units 26 is stopped. As the sleeve moving unit 24 serving as the nut stops, the sleeve 25, which has been only rotating, can start to move while rotating, thereby rotating and moving the cutter 31.

Accordingly, the structure can reduce start load since load is not applied directly to the motor during a period of time in which the sleeve moving unit 24 moves by the gap as described above.

The shaft guide surfaces 25-4 moves, while sliding, along the inner surface of the shaft of the variable shaft gear 21. The spline shaft is provided by setting the length of the shaft guide surfaces 25-4 to be equal to the distance of the movement of the cutter 31. The variable shaft gear 21 serves as the spline boss. The cutter 31 connected to the sleeve 25 performs a unique function thereof, i.e. excising a tissue of a living body, while advancing or retreating in response to the sliding of the sleeve 25. In addition, when the motor rotates in the opposite direction, the operation is performed in a reverse manner, so that the sleeve moving unit 24, which has only been rotating, rotates and moves by the gap of the opposite sleeve support unit 26, thereby sliding in the opposite direction.

In addition, the free ends 25-2 and 25-3 are provided on both ends of the screw 25-1 of the sleeve 25. The free ends 25-2 and 25-3 are defined by circular grooves provided on end portions of the thread ridge, corresponding to the width of a single pitch of the thread, in place of the thread ridge. The pitch of the free ends is 0. When the groove of the screw 25-1 reaches one free end of the free ends 25-2 and 25-3 during the rotation of the screw 25-1 about the ball 24-3, the ball 24-3 idles on the free end. Even in a case in which the motor 12 rotates, the sleeve 25 idles without movement, no load is applied to the motor, and the movement of the sleeve 25 is stopped. Accordingly, the movement of the sleeve 25 is limited by a smaller one of the length of the shaft guide surfaces 25-4 and the length of the screw 25-1. The length of the screw 25-1 may be determined to be smaller than the length of the shaft guide surfaces 25-4 to reduce the load of the motor.

In addition, in a situation in which the ball 24-3 is located on one free end of the free ends 25-2 and 25-3 due to the omnidirectional rotation of the motor, the idling is continued in a case in which the motor 12 is restarted and the axial rotation direction of the motor is a direction in which the sleeve 25 moves along the corresponding free end. If the motor rotates in the opposite direction, the compression spring 26-3, i.e. an elastic member of the sleeve support unit 26, causes the ball 24-3 to reenter the groove of the screw after having rotated on the free end. The sleeve moving unit 24 stops after having moved together with the ball 24-3 in the opposite direction, by the gap between the spring guide 26-1 and the spring guide 26-2, but the sleeve 25 continuously moves. Although the axial position of the ball 24-3 is fixed, the sleeve 25 rotates and moves along the groove of the screw 25-1 while being supported by the ball 24-3. If the sleeve 25 has started from one free end, e.g. the free end 25-2, the sleeve 25 reaches the opposite free end, e.g. the free end 25-3. In addition, in the opposite sleeve support unit 26, the two spring guides 26-1 and 26-2, which have been spread, are compressed (or contracted) again by the compression spring 26-3 when the direction of the rotation of the motor is converted. When the spring guides 26-1 and 26-2 are in contact, the sleeve 25, which has been rotating in a fixed position, is caused to rotate and slide. Accordingly, in this case, the motor 12 moves the sleeve moving unit 24 in an early stage and then pushes the opposite sleeve support unit 26. Here, load due to the elastic force of the compression spring 26-3 may be applied to portions corresponding to the distances by which the two spring guides 26-1 and 26-2 are spread by the compression springs 26-3 of the sleeve support units 26, and in the early stage, the motor 12 may rotate without load by which the sleeve 25 is pushed. In addition, when the gap between the spring guide 26-1 and the spring guide 26-2 is removed, the sleeve 25, which has been rotating in a fixed position, advances or retreats to be subjected to the load at this point in time, thereby reducing the start load of the motor 12 in the early stage. A motor may produce noise and vibration when the initial load is strong.

According to the present invention, the gap is provided by the distance between the spring guides 26-1 and 26-2, thereby obtaining an effect of blocking any load from being applied to the start load of the motor during the time period in which the gap is reduced. During the time period in which the gap is reduced, only the load corresponding to the elastic force of the springs may be applied, thereby significantly reducing the initial start load of the motor. Thus, in a case in which the elastic force of the compression spring 26-3 is reduced so that the two spring guides 26-1 and 26-2 are spread and the ball on the free end may reenter the groove of the screw in the direction change between advancement and retreat, the biopsy needle assembly able to reduce starting load according to the present invention can be provided. That is, when the sleeve 25 rotates with respect to the sleeve moving unit 24, one sleeve support unit 26 of the sleeve support units 26, directed opposite to the direction of the movement, overcomes the elastic force of the compression spring 26-3 therewithin, due to the pressure of the sleeve moving unit 24, thereby removing the gap between the spring guide 26-1 and the spring guide 26-2. In the sleeve support unit 26 disposed opposite to the above-described sleeve support unit 26 with respect to the sleeve moving unit 24, the spring guide 26-1 and the spring guide 26-2 are spread by the compression spring 26-3 disposed within the sleeve support unit 26, thereby forming the gap. When the motor rotates in the opposite direction in the situation in which one sleeve support unit 26 moves without the gap, the sleeve 25 rotates in the opposite direction with respect to the sleeve moving unit 24. In contrast, the gap between the spring guide 26-1 and the spring guide 26-2 is removed, due to the elastic force of the compression spring 26-3 within the opposite sleeve support unit 26 moving due to the pressure of the sleeve moving unit 24 being overcome. In addition, in the other sleeve support unit 26 disposed opposite with respect to the sleeve moving unit 24, the spring guide 26-1 and the spring guide 26-2 are spread by the compression spring 26-3 disposed within the sleeve support unit 26, and the gap is formed again.

In addition, according to the present invention, the sleeve moving unit 24 is a component having the shape of a hollow cylinder, and mechanically coupled to the screw 25-1. The sleeve moving unit 24 is provided with the ball 24-3 serving as a screw or a thread ridge of other gears. The screw 25-1 is supported by the ball 24-3. When the sleeve 25 rotates, the sleeve moving unit 24 is trapped by the sleeve support units 26 provided on both ends thereof. The sleeve 25 advances or retreats while rotating. The cutter 31 coupled to the sleeve 25 advances and retreats while rotating, thereby excising a tissue.

The two sleeve support units 26 may be disposed on both sides of the sleeve moving unit 24. Each of the sleeve support units 26 is movable while the length thereof is varied by the sleeve moving unit 24. As illustrated in FIG. 5, the sleeve 25 extends through the two sleeve support units 26 together with the sleeve moving unit 24. As described above, each of the sleeve support units 26 includes two spring guides 26-1 and 26-2 disposed on both sides of the compression spring 26-3. The spring guides 26-1 and 26-2 have cylindrical portions extending into the compression spring 26-3 with a predetermined distance and end portions supporting the compression spring 26-3. When no external force is applied, the gap between the two spring guides 26-1 and 26-2 is increased by the compression spring 26-3, as in the case of the left sleeve support unit 26. As in the case of the right sleeve support unit 26, power, or force, transmitted from the motor 12 overcomes the elastic force of the compression spring 26-3, so that the spring guides 26-1 and 26-2 are in contact with each other, with no gap being present therebetween. When the motor rotates in the opposite direction, the two spring guides 26-1 and 26-2 on the left side move again in contact with each other. The sleeve support units 26 as described above are disposed on the outer surface of the sleeve 25, on both sides of the sleeve moving unit 24. When the sleeve moving unit 24 is only movable by the gap between the spring guides 26-1 and 26-2 of the sleeve support unit 26 but is not movable beyond the gap, the sleeve 25 moves. That is, the sleeve support unit 26 is supported by the supports 22-1 and 22-2, thereby allowing the sleeve 25 to move.

Figure 7:
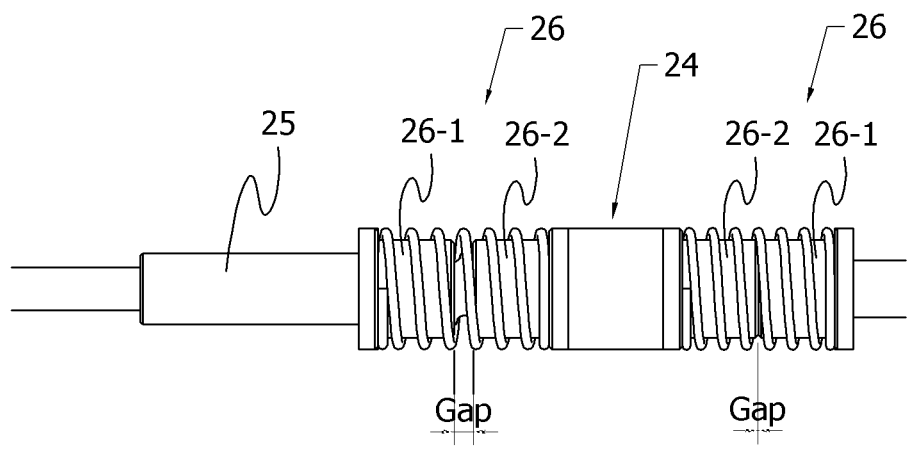
FIG. 7 is a view illustrating the sleeve moving unit and the sleeve support units coupled to the sleeve.
Figure 8:
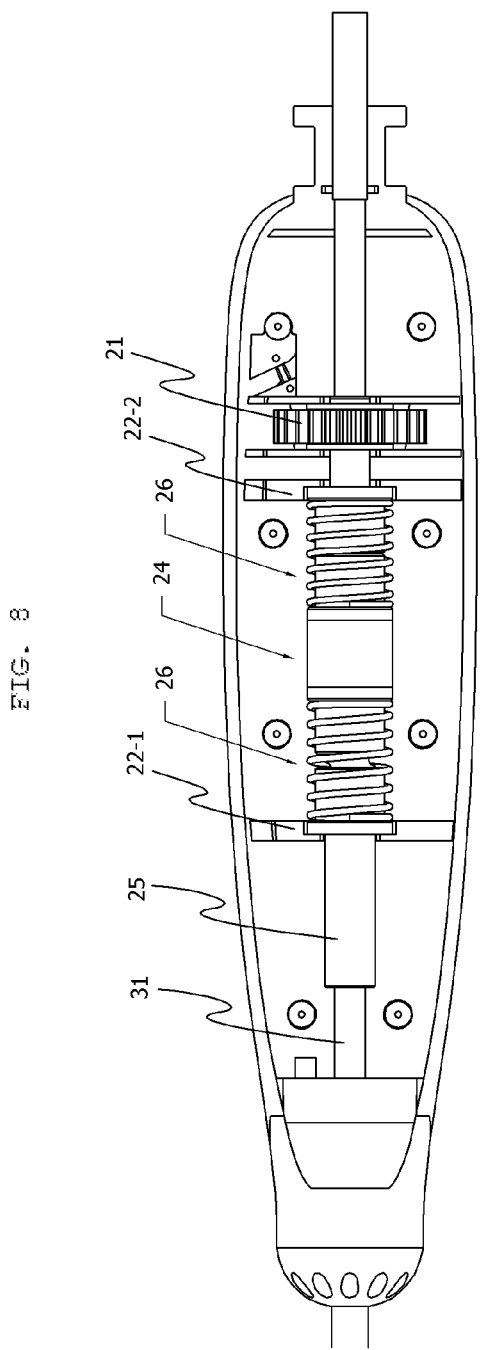
FIG. 8 is a view illustrating an assembly of the sleeve, illustrated in FIG. 7, being seated on a biopsy needle assembly.

FIG. 7 is a view illustrating the sleeve moving unit 24 and the sleeve support units 26 coupled to the sleeve 25, and FIG. 8 is a view illustrating an assembly of the sleeve 25, illustrated in FIG. 7, being seated on a biopsy needle assembly. The rotation of the variable shaft gear 21 causes the sleeve support units 26 to be pushed with respect to the ball 24-3 of the sleeve moving unit 24 and are fixed by the supports 22-1 and 22-2. The spring guides 26-1 and 26-2 on the right side come into contact with each other by overcoming the elastic force of the compression spring 26-3, thereby removing the gap between the spring guides 26-1 and 26-2. Then, the sleeve 25 moves to the left while rotating, and the cutter 31 also moves to the left. In addition, the gap between the spring guides 26-1 and 26-2 on the left side is increased by the elastic force of the compression spring 26-3, as illustrated in FIG. 8. When the motor rotates in the opposite direction from this position, the gap between the spring guides 26-1 and 26-2 on the left side is removed, and the gap between the spring guides 26-1 and 26-2 on the right side is increased. The sleeve 25 and the cutter 31 move, while rotating, in the opposite direction. Here, the size of the gap may be substantially the same as one pitch of the screw, and may be determined to be approximately in the range from 1 to 5 mm.

The sleeve 25 and the cutter 31 may be completely coupled by welding or the like. The cutter 31 may be interference-fitted into the sleeve 25. Alternatively, the sleeve 25 and the cutter 31 may be coupled via screw engagement. The length of the shaft guide surfaces of the sleeve 25 is the maximum length of actual sliding, and limits the distance to which the cutter moves. The shaft size of the variable shaft gear 21 may be determined depending on the shaft guide surfaces 25-4. When the portions in which the shaft guide surfaces 25-4 are formed have the shape of a half moon, the shaft may have the shape of a half moon. When both side portions of the cylinder are cut surfaces, the shaft may be formed to conform thereto.

The sleeve may have a function of supporting the spring support ends of the spring guides 26-1 of the sleeve support units 26 are seated on and supported by the supports 22-1 and 22-2 and a function of supporting the sleeve moving unit 24 and the two sleeve support units 26 while limiting the distances of the movement of the sleeve moving unit 24 and the two sleeve support units 26. The length may be determined to be a length measured when the elastic member of one of the sleeve support units 26 is compressed and the elastic member of the other sleeve support unit 26 is relaxed.

In addition, the gear supports 22-3 and 22-4 simply serve to support the shaft while limiting the movement of the variable shaft gear 21. In general, as illustrated in the drawings, the supports 22 may be formed integrally with the interior of the biopsy needle assembly 2 by plastic molding, or may be fabricated separately to serve as a support. The supports 22 are required to be finally fixed by the biopsy needle assembly 2 to perform the intended function.

Figure 9:
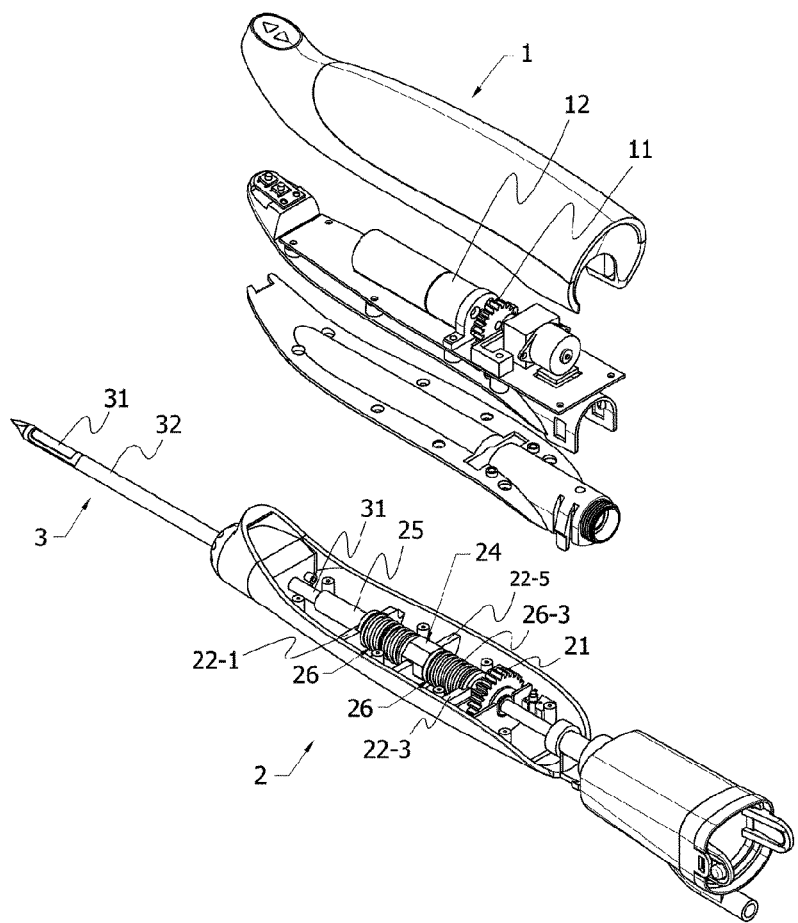
FIG. 9 is an exploded perspective view illustrating the biopsy needle assembly according to the present invention, from which the body (or motor unit) is separated.
Figure 10:
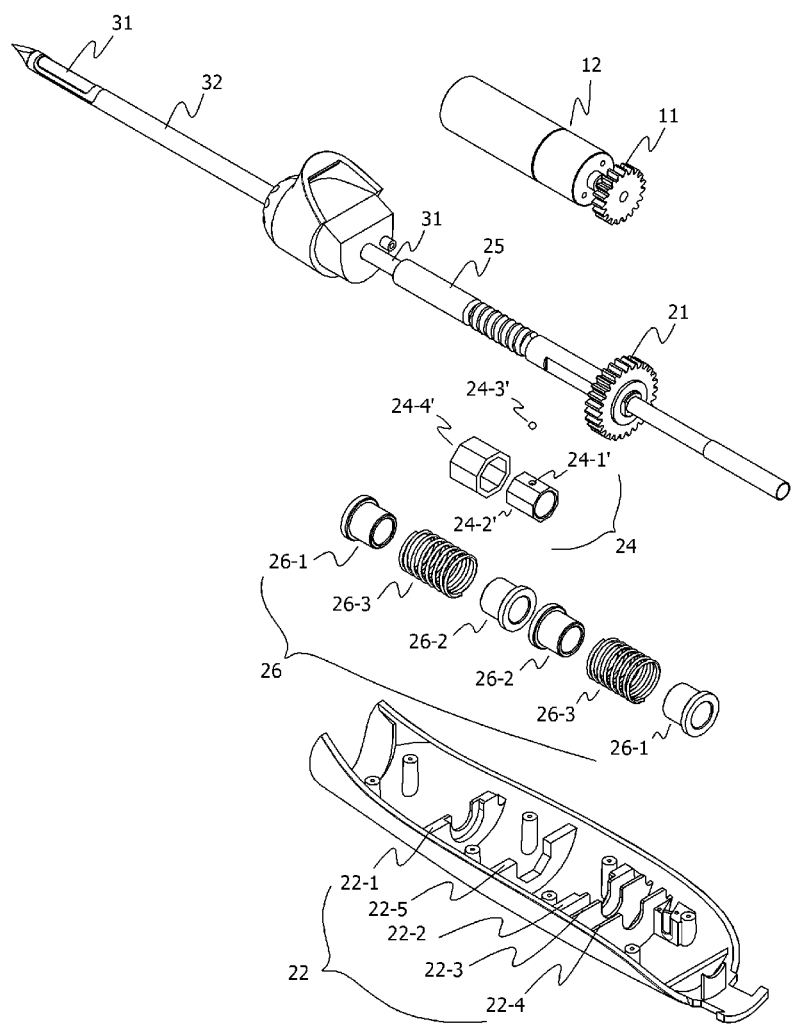
FIG. 10 is an exploded perspective view separately illustrating power transmitting components in FIG. 9.
Figure 11:
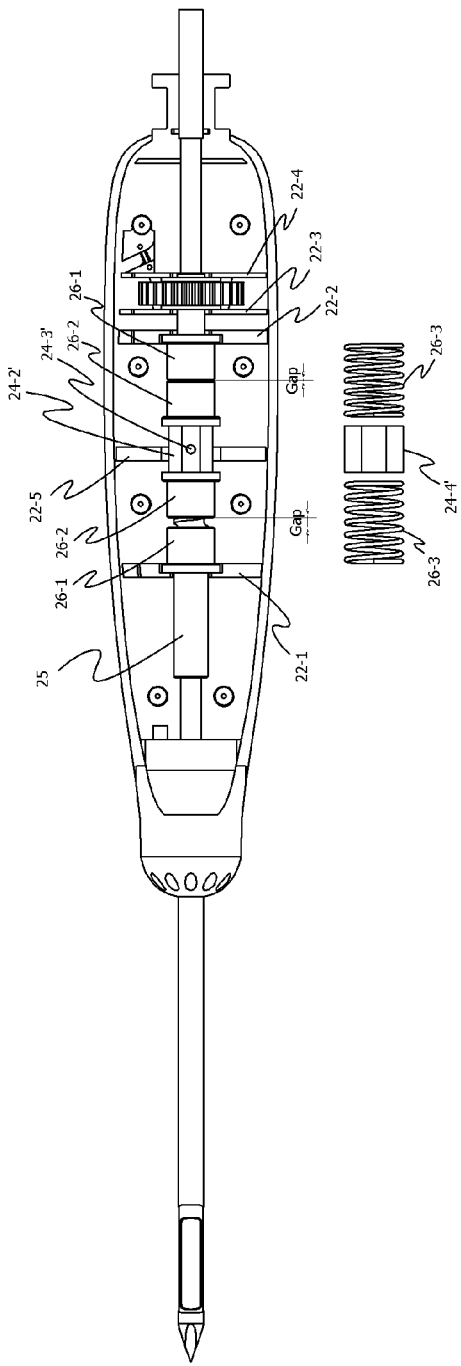
FIG. 11 is an assembled view illustrating the sleeve assembly, illustrated in FIG. 9, is seated in the biopsy needle assembly.

FIGS. 9 to 11 illustrate a biopsy needle assembly according to a second embodiment of the present invention, in which a different sleeve moving unit is provided. FIG. 9 is an exploded perspective view illustrating the biopsy needle assembly according to the present invention, from which the body (or motor unit) is separated, FIG. 10 is an exploded perspective view separately illustrating power transmitting components in FIG. 9, and FIG. 11 is an assembled view illustrating the sleeve assembly, illustrated in FIG. 9, is seated in the biopsy needle assembly.

In the sleeve moving unit 24 according to the first embodiment described above with reference to FIGS. 3 to 8, a coupling method, such as bonding, is required to allow the support holder 24-2 and the fixing holder 24-4 supporting the ball 24-3 to axially advance and retreat by the gap while being supported by the sleeve support units 26 and the supports 22-1 and 22-2. The sleeve moving unit 24 illustrated in FIGS. 9 to 11 is configured such that a fixing holder 24-4' supported by the fixing holder support 22-5 cannot rotate while being able to advance/retreat, and that a support holder 24-2' sliding-coupled to the fixing holder 24-4' cannot rotate while being able to advance/retreat. The fixing holder support 22-5 is attached to a housing together with other supports or is fabricated integrally with the housing to serve to limit the ball 24-3 so that the ball 24-3 does not rotate together with the screw 25-1. In addition, according to the present embodiment, the sleeve moving unit 24 is prevented from rotating by the fixing holder support 22-5, and is allowed to advance or retreat by the sleeve support units 26 moving in an advancing/retreating direction by the gap in response to the rotation of the screw 25-1.

As described above, the second embodiment illustrated in FIGS. 9 to 11 is configured such that the sleeve moving unit 24 is not rotatable and the sleeve 25 rotates about a ball 24-3' of the sleeve moving unit 24. The same principle is applied to the operation of the other components, including the sleeve 25 and the sleeve support units 26, as in the embodiment illustrated in FIGS. 3 to 8.

In the second embodiment of the present invention, the fixing holder 24-4' of the sleeve moving unit 24 has the shape of an octagonal pipe. That is, the outer cross-section and the inner cross-section of the fixing holder 24-4' are octagonal. The fixing holder support 22-5 is additionally provided as one component of the supports 22 to conform to the octagonal shape of the outer surface of the fixing holder 24-4', thereby supporting the fixing holder 24-4'. In addition, the cross-section of the outer surface of the support holder 24-2' is octagonal to conform to the inner surface of the fixing holder 24-4', and the cross-section of the inner surface of the support holder 24-2' is circular to conform to the sleeve 25. In the present embodiment, all of the octagonal cross-section portions may be substituted with any other shape, such as a polygonal shape or an elliptical shape, which can restrain rotation when supported by the fixing holder support 22-5. In addition, when the cross-sections of the support holder 24-2' and the fixing holder 24-4' are circular, a protrusion or a recess may be provided. In this case, when the rotation is restrained by the fixing holder support 22-5, the same operation may be enabled. That is, the sleeve moving unit 24 is supported by the fixing holder support 22-5 so as to be linearly movable, e.g. advancement and retreat, without being able to rotate. Consequently, the ball 24-3' does not rotate, and the screw 25-1 of the sleeve 25 can rotate about the ball. Accordingly, when the screw 25-1 of the sleeve 25 is rotated by the motor, the needle 3 can advance or retreat with respect to the ball depending on the direction of rotation. In addition, the sleeve 25 is provided with the screw 25-1, and the screw 25-1 is provided with the free ends 25-2 and 25-3 on both ends of the screw 25-1. The free ends 25-2 and 25-3 can idle about the ball to reduce load. When the direction of the rotation of the motor changes, the ball escapes the free end through the sleeve support unit 26. Consequently, the opposite rotation is performed about the ball along the groove of the screw 25-1 of the sleeve 25, so that the needle 3 can move linearly in the opposite direction. Accordingly, as a difference from the embodiment illustrated in FIGS. 3 to 8, the fixing holder support 22-5 is additionally provided to prevent the rotation of the sleeve moving unit 24. Then, the rotation of all of the ball 24-3, the support holder 24-2' supporting the ball, and the fixing holder 24-4' fixing the support holder 24-2' is restrained by the fixing holder support 22-5. In a case in which the ball 24-3 or 24-3' is fixed without rotating around the screw 25-1, it is possible to support the ball 24-3 or 24-3' by only the support holder 24-2 or 24-2' without the fixing holder 24-4 or 24-4'. In addition, the support holder 24-2 or 24-2' may be provided with a protrusion shape and a function similar to those of the ball, so that the sleeve moving unit 24 can be used as a single component. However, if the sleeve moving unit is an integral unit, it may be difficult to attach the sleeve moving unit to the screw unit or detach the sleeve moving unit from the screw unit. Thus, the sleeve moving unit may be provided as an assembly of two or more components as in the second embodiment, instead of being provided as an integral unit. If the sleeve moving unit is provided as a single integral component, the sleeve moving unit may be provided as an assembly of two pieces to be attached to one end portion of the screw unit, in consideration of assembly. One of the two pieces may be screw-engaged with the screw portion together with the ball of the sleeve moving unit, and the other piece may be finally coupled to the screw portion, such that the sleeve and the sleeve moving unit may be fabricated and used as illustrated.

According to the major feature of the principle of the operation of the first embodiment and the second embodiment of the present invention, the sleeve having the screw is rotated about the ball or protrusion of the sleeve moving unit serving as the nut, such that the sleeve can perform a linear movement, such as advancement and retreat, while being able to rotate. In addition, the free ends are provided on both ends of the screw. The pair of sleeve support units and the sleeve moving unit provided between the sleeve support units press the ball so that the ball does not escape the free end when the direction of the rotation of the motor is converted. According to this configuration, the sleeve is movable axially due to the rotation of the screw of the sleeve.

Accordingly, the above-described ball 24-3 or 24-3' may be substituted with a variety of protrusions or recesses corresponding to the thread of the screw 25-1, and the fixing holder and the support holder may be configured to allow the screw to rotate about the ball or protrusion. In such a situation, the major principle of the operation of the present invention may be applied in the same manner.

Figure 12:
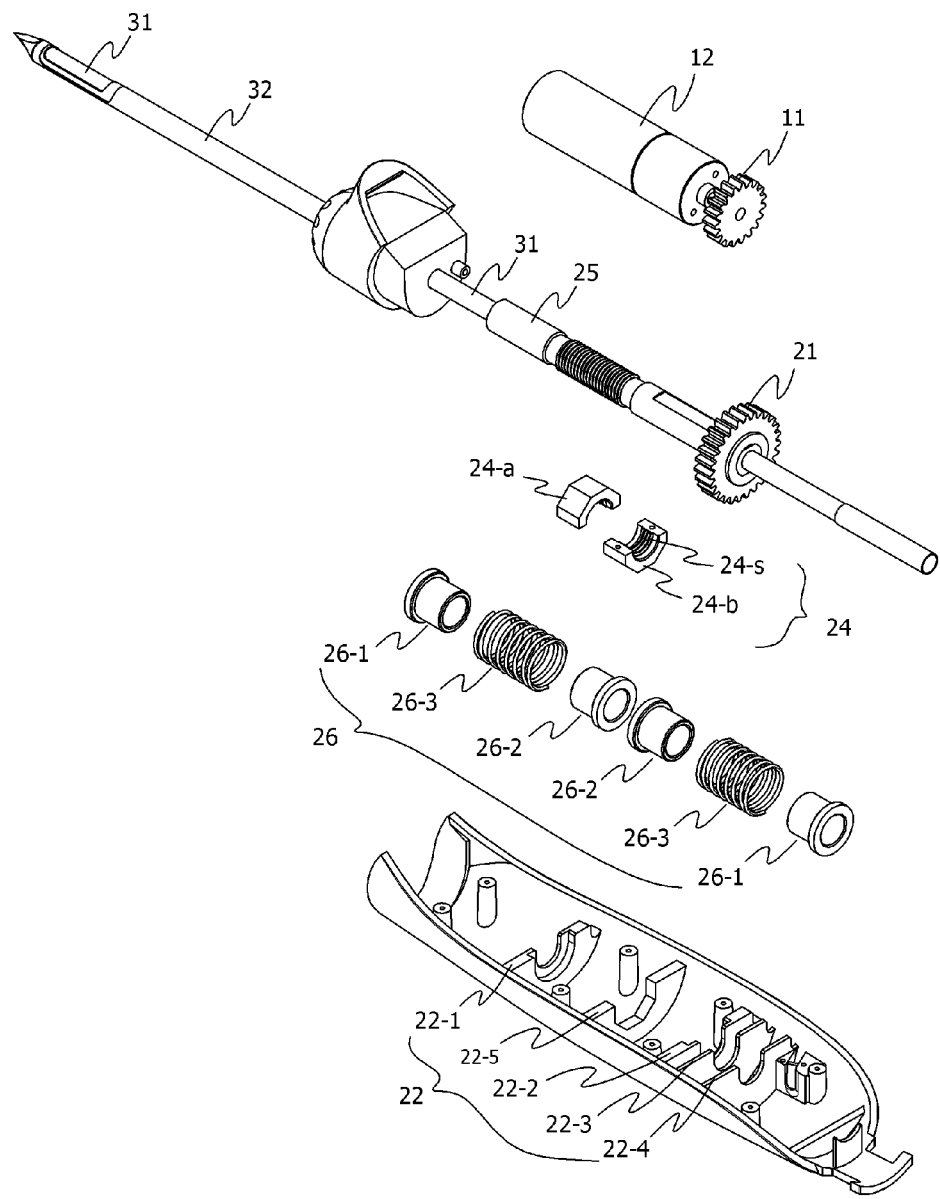
FIG. 12 is an exploded perspective view illustrating separately illustrating power transmitting components.
Figure 13:
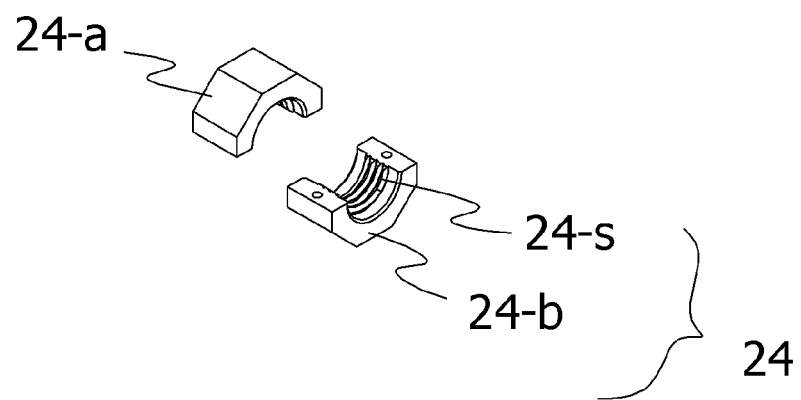
FIG. 13 is an enlarged view of the sleeve moving unit illustrated in FIG. 12.
Figure 14:
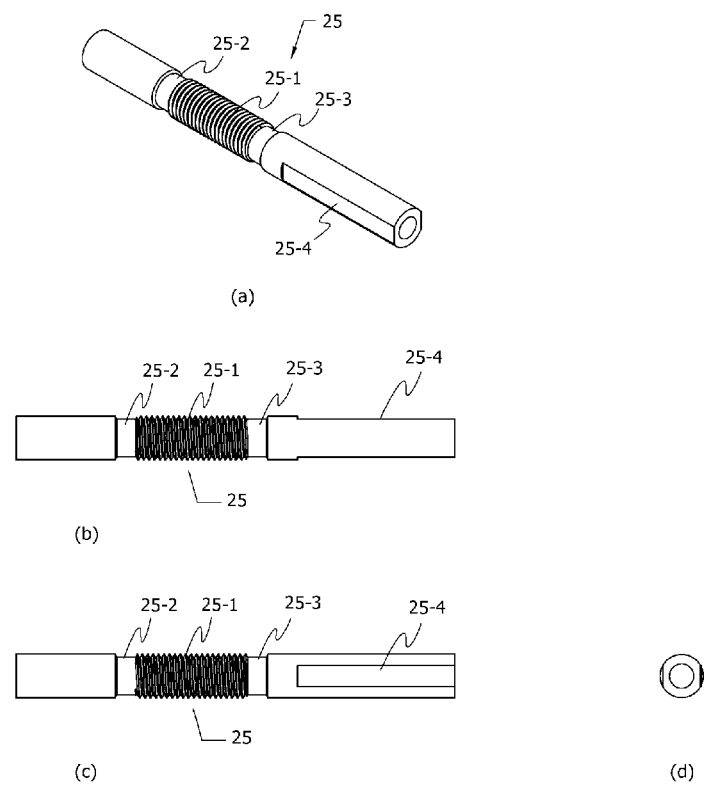
FIG. 14 illustrates a perspective shape, a top shape, a front shape, and a side shape of the sleeve used in the present embodiment.

FIGS. 12 to 14 illustrate a biopsy needle assembly according to a third embodiment of the present invention, in which the sleeve moving unit 24 is different from that of the above-described second embodiment. FIG. 12 is an exploded perspective view illustrating separately illustrating power transmitting components, FIG. 13 is an enlarged view of the sleeve moving unit illustrated in FIG. 12, and FIG. 14 illustrates a perspective shape (a), a top shape (b), a front shape (c), and a side shape (d) of the sleeve used in the present embodiment.

As illustrated in FIGS. 12 to 14, the biopsy needle assembly according to the third embodiment of the present invention is substantially the same as the needle assembly according to the second embodiment, except for specific configurations of the biopsy needle assembly and the sleeve moving unit 24, as well as the sleeve 25. Thus, in the third embodiment, the sleeve moving unit 24 and the sleeve 25 may mainly be described. As described above in the first and second embodiments, the sleeve moving unit 24 serves as a nut corresponding to the screw 25-1 of the sleeve 25. The sleeve moving unit 24 is only comprised of fixing holders 24-a and 24-b respectively being provided with a thread 24-s therein, modified from the fixing holder 24-4' according to the second embodiment as described above. As illustrated in FIGS. 13 and 14, the fixing holder according to the third embodiment is configured such that the upper fixing holder 24-a and the lower fixing holder 24-b are coupled to each other. The upper fixing holder 24-a and the lower fixing holder 24-b are respectively provided the thread 24-s therein to serve as nuts, the thread 24-s corresponding to the screw 25-1 of the sleeve 25. In FIGS. 13 and 14, the fixing holders are provided as separate upper and lower pieces to be easily coupled to the screw 25-1 of the sleeve 25. The fixing holders are coupled to each other to provide the single sleeve moving unit 24. However, this is merely provided for the sake of convenience, but the thread 24-s may be provided in the inner surface of a single fixing holder. The supporting principle and operation of the fixing holders 24-a and 24-b are the same as those of the second embodiment, except that the thread 24-s is provided to substitute for the ball 24-3 or 24-3'. The fixing holders 24-a and 24-b also have an octagonal outer shape, and are supported by the fixing holder support 22-5.

The sleeve according to the third embodiment illustrated in FIG. 14 differs from the sleeve according to the first embodiment illustrated in FIG. 6, in that the free ends 25-2 and 25-3 have different widths (or sizes). According to the first and second embodiments, the sleeve moving unit uses the ball 24-3 or 24-3' and the sizes of the free ends may be as small as the diameter of the ball. In contrast, in the third embodiment, the sizes of the free ends are determined depending on the width of the thread 24-s of the sleeve moving unit 24, and thus, are wider than that of the first or second embodiment. That is, the widths are determined such that the thread 24-s can freely rotate without load on the free ends 25-2 and 25-3.

Also in the sleeve moving unit 24 according to the third embodiment, the thread 24-s serves as the ball 24-3 or 24-3' to define the gap together with the sleeve support units 26 to reduce the load of the motor, thereby preventing impact to the needle, when the direction of the rotation of the motor is converted.

Figure 15:
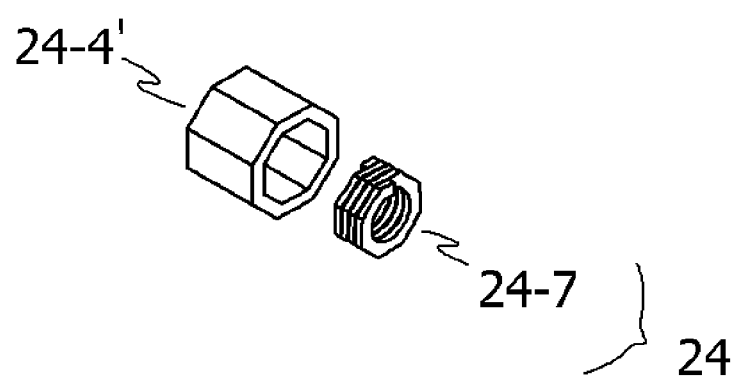
FIG. 15 is an exploded perspective view separately illustrating components of the sleeve moving unit according to a fourth embodiment of the present invention.

FIG. 15 is an exploded perspective view separately illustrating components of the sleeve moving unit 24 in a biopsy needle assembly according to a fourth embodiment of the present invention, different from the third embodiment.

According to the fourth embodiment, a coil-shaped thread spring 24-7, such as a compression spring, is inserted into the fixing holder 24-4 or 24-4' according to the first embodiment or the second embodiment to serve as a thread of the fixing holder, thereby forming the sleeve moving unit 24. Here, the outer cross-section of the thread spring 24-7 has an octagonal shape corresponding to the octagonal shape of the inner cross-section of the fixing holder 24-4', both the outer cross-section and the inner cross-section of which are octagonal. Thus, the thread spring 24-7 is supported on the inner surface of the fixing holder 24-4' so as not to be rotated. The sleeve according to the fourth embodiment has free ends, the sizes of which are substantially equal to the width of the thread spring 24-7, like the free ends 25-2 and 25-3. The thread spring 24-7 according to the fourth embodiment has a configuration in which the ball 24-3' is coupled to the through-hole 24-1' of the support holder 24-2' according to the second embodiment.

The biopsy needle assembly having a structure by which the starting load of the motor may be used in a variety of manners according to the above described features by a person having ordinary skill in the art.

INDUSTRIAL APPLICABILITY

The biopsy needle assembly according to the present invention is mainly usable as a medical device while being usable in related and similar industrial fields. That is, the biopsy needle assembly may be used in a field in which forward rotation and backward rotation are used alternatingly when the biopsy needle assembly is inserted into an object and extracts an incised portion of the object.

The invention claimed is:

1. A biopsy needle assembly used in a biopsy device, the biopsy device including:
   a body controlling a motor and a vacuum pressure;
   a biopsy needle assembly receiving rotational power from the body; and
   a needle provided on a distal end of the biopsy needle assembly to extend from a cutter that incises a tissue,
   the biopsy needle assembly comprising:
   a gear unit including a fixed shaft gear and a variable shaft gear transmitting the rotational power of the motor;
   a sleeve including one portion connected to a central portion of the variable shaft gear to serve as a shaft of the variable shaft gear, the other portion connected to the cutter, and a thread-shaped screw provided on an outer surface of an intermediate portion between one portion and the other portion of the sleeve;
   a sleeve moving unit corresponding to a thread of the screw to serve as a nut of the screw to linearly move the sleeve in forward and backward directions;
   a pair of sleeve supporting units respectively including a compression spring and a pair of spring guides disposed on both sides of the compression spring to face each other, the spring guides defining a gap therebetween due to elastic force of the compression spring to prevent the compression spring from being in contact with the screw, wherein the pair of sleeve supporting units is fitted around outer surface portions of the sleeve and disposed on both sides of the sleeve moving unit such that the sleeve supporting units face each other; and
   a gear support allowing the variable shaft gear to rotate without advancing or retreating and a support supporting and restraining the sleeve moving unit and the sleeve supporting units to be axially movable in a range of the gap between the spring guides defined by the compression spring in a situation in which the sleeve is inserted into the sleeve moving unit and the sleeve supporting units on both sides of the sleeve moving unit, wherein the sleeve advances or retreats while rotating about the sleeve moving unit in response to rotation of the gear unit, and one sleeve supporting unit of the sleeve supporting units, to which a direction of rotation of the motor is converted, delays the advancement or retreat of the sleeve by the gap between the spring guides defined by the compression spring, thereby reducing starting load of the motor.

2. The biopsy needle assembly according to claim 1, wherein the sleeve moving unit linearly moves in response to the screw of the sleeve, and the sleeve moving unit includes a ball or a thread to correspond to the screw to serve as a nut corresponding to the screw, the sleeve moving unit being configured so that the ball or the thread does not escape the screw even when the sleeve rotates.

3. The biopsy needle assembly according to claim 2, wherein the sleeve moving unit includes a fixing holder having a rectangular, elliptical, or polygonal cross-sectional shape, the fixing holder being supported by the support so as not to rotate, and a barrel-shaped support holder having a cylindrical, polygonal, or elliptical outer cross-sectional shape having a protrusion or a recess, with a through-hole being provided in a surface portion of the barrel-shaped support holder, and a ball inserted into the through-hole, wherein the fixing holder surrounds the support holder and the ball so that the support holder does not rotate along the outer cross-sectional shape of the support holder in a situation in which the ball is inserted into the through-hole;

a thread is provided directly on an inner surface of the fixing holder; or a thread spring is inserted into the fixing holder, the thread spring having an outer shape corresponding to the inner surface of the fixing holder; and the support further includes a fixing holder support disposed on an inner surface of a housing of the biopsy needle assembly to restrain rotation of the fixing holder.

4. The biopsy needle assembly according to claim 1, wherein the sleeve has a shaft guide surface provided on one portion and a pipe-shaped one end of the cutter provided on the opposite portion, when the central portion of the variable shaft gear is inserted into the shaft guide surface to rotate the variable shaft gear, the sleeve and the cutter rotate and move together, and free ends having a zero pitch are provided on both ends of the screw, and when the sleeve moving unit serving as the nut is inserted into the screw to rotate the sleeve, the sleeve is rotated and moved by a pitch of the screw, and the sleeve rotates without moving on the free ends having the zero pitch of the screw.

5. The biopsy needle assembly according to claim 1, wherein the gear support allowing the variable shaft gear to rotate without movement and the support supporting and restraining the sleeve moving unit and the sleeve supporting units to be axially movable in a range of the gap between the spring guides defined by the compression spring are provided integrally with an inner surface of a housing of the biopsy needle assembly.

6. The biopsy needle assembly according to claim 1, wherein the sleeve supporting units respectively include the compression spring and spring guides respectively having an end portion in contact with one end of both ends of the compression spring and a barrel-shaped portion inserted into the compression spring, the spring guides being fitted around the outer surface of the sleeve.

\* \* \* \* \*